United States Patent
Gasser et al.

(10) Patent No.: US 7,175,430 B1
(45) Date of Patent: Feb. 13, 2007

(54) SUPPORT MATERIALS AND IMAGING METHOD FOR INTRAORAL DIAGNOSTIC PURPOSES

(75) Inventors: Oswald Gasser, Seefeld (DE); Rainer Guggenberger, Herrsching (DE); Bernd Gangnus, Andechs (DE); Ingo Häberlein, Weilheim (DE)

(73) Assignee: 3M ESPE AG, Seefeld (DE)

( * ) Notice: Subject to any disclaimer, the term of this patent is extended or adjusted under 35 U.S.C. 154(b) by 554 days.

(21) Appl. No.: 10/009,603

(22) PCT Filed: Jun. 13, 2000

(86) PCT No.: PCT/EP00/05418

§ 371 (c)(1),
(2), (4) Date: Dec. 11, 2001

(87) PCT Pub. No.: WO01/12237

PCT Pub. Date: Feb. 22, 2001

(30) Foreign Application Priority Data

Jun. 11, 1999 (DE) ................................ 199 26 728

(51) Int. Cl.
*A61C 9/00* (2006.01)
*A61K 49/00* (2006.01)
*C12Q 1/14* (2006.01)

(52) U.S. Cl. ........................ 433/37; 433/215; 600/362; 424/9.7; 435/36

(58) Field of Classification Search .................. 433/37, 433/71, 72, 215; 600/362; 424/9.7, 9.71; 435/36
See application file for complete search history.

(56) References Cited

U.S. PATENT DOCUMENTS

| | | | |
|---|---|---|---|
| 3,255,079 A | | 6/1966 | Schroeder et al. |
| 3,309,274 A | * | 3/1967 | Brilliant ...................... 424/9.6 |
| 3,453,242 A | | 7/1969 | Schmitt et al. |
| 3,507,269 A | * | 4/1970 | Berry .......................... 600/367 |
| 3,634,400 A | | 1/1972 | Schmitt et al. |
| 3,897,376 A | | 7/1975 | Lampe |
| 3,903,252 A | * | 9/1975 | Stearns et al. .............. 424/9.71 |
| 3,959,881 A | * | 6/1976 | Kokal, Jr. .................... 433/70 |
| 4,035,453 A | | 7/1977 | Hittmair et al. |
| 4,093,555 A | | 6/1978 | Schmitt et al. |
| 4,167,618 A | | 9/1979 | Schmitt et al. |
| 4,302,439 A | | 11/1981 | Selwyn |
| 4,354,535 A | | 10/1982 | Powell et al. |
| 4,368,272 A | * | 1/1983 | Kashket ...................... 600/572 |
| 4,397,944 A | * | 8/1983 | Komura et al. ................ 435/4 |
| 4,459,277 A | * | 7/1984 | Kosti ........................ 424/9.71 |
| 4,532,268 A | | 7/1985 | Jochum et al. |
| 4,582,795 A | * | 4/1986 | Shibuya et al. ............... 435/34 |
| 4,666,700 A | * | 5/1987 | Frysh ........................ 424/9.71 |
| 4,877,854 A | | 10/1989 | Hattori et al. |
| 4,976,951 A | * | 12/1990 | Rosenberg et al. ......... 435/7.32 |
| 4,992,256 A | * | 2/1991 | Skaggs et al. ............. 424/9.71 |
| 5,086,148 A | | 2/1992 | Jochum et al. |
| 5,190,743 A | * | 3/1993 | Simone et al. ............. 424/9.71 |
| 5,357,989 A | * | 10/1994 | Gathani ....................... 132/321 |
| 5,395,239 A | * | 3/1995 | Komatsu et al. .............. 433/68 |
| 5,422,093 A | | 6/1995 | Kennedy et al. |
| 5,563,124 A | | 10/1996 | Damien et al. |
| 5,569,691 A | | 10/1996 | Guggenberger et al. |
| 5,665,559 A | | 9/1997 | Simonson |
| 5,725,373 A | | 3/1998 | Yeh |
| 5,849,812 A | | 12/1998 | Zech et al. |
| 5,981,300 A | * | 11/1999 | Moll et al. .................... 422/57 |
| 6,051,249 A | | 4/2000 | Samuelsen |
| 6,084,005 A | * | 7/2000 | Fukunishi et al. .......... 523/105 |
| 6,197,331 B1 | | 3/2001 | Lerner et al. |
| 6,599,974 B1 | | 7/2003 | Bublewitz et al. |
| 6,699,040 B1 | | 3/2004 | Hahn et al. |
| 6,860,879 B2 | | 3/2005 | Irion et al. |
| 6,894,144 B1 | | 5/2005 | Zech et al. |
| 2001/0016760 A1 | | 8/2001 | Irion et al. |
| 2003/0060719 A1 | | 3/2003 | Irion et al. |
| 2003/0153726 A1 | | 8/2003 | Eckhardt et al. |
| 2004/0042960 A1 | | 3/2004 | Frey et al. |
| 2004/0248058 A1 | | 12/2004 | Hahn et al. |
| 2004/0248061 A1 | | 12/2004 | Hahn et al. |

(Continued)

FOREIGN PATENT DOCUMENTS

DE 914 325 C 7/1954

(Continued)

OTHER PUBLICATIONS

Yamamoto, et al.: Database accession No. 131:144857, XP002156957.

(Continued)

*Primary Examiner*—Ralph A. Lewis
(74) *Attorney, Agent, or Firm*—Mueting, Raasch & Gebhardt, P.A.

(57) ABSTRACT

The invention relates to deformable, curable or film-forming support materials which contain diagnostically useful additives for locus- and substance-specific intraoral diagnostics, and processes for the preparation of images for intraoral locus- and substance-specific diagnostic purposes, in which diagnostically useful additives are applied to deformable, curable or film-forming support materials containing no diagnostically useful additives, in such a quantity that a diagnostic signal can be observed, the diagnostic result being obtained without a cultivation step.

28 Claims, No Drawings

U.S. PATENT DOCUMENTS

2004/0248062 A1    12/2004    Hahn et al.

FOREIGN PATENT DOCUMENTS

| | | |
|---|---|---|
| DE | 17 45 810 A | 1/1970 |
| DE | 17 45 810 PS | 1/1970 |
| DE | 25 15 593 | 10/1975 |
| DE | 25 15 593 C2 | 7/1982 |
| DE | 37 41 575 A1 | 6/1988 |
| DE | 37 43 983 C2 | 7/1988 |
| DE | 38 38 587 A | 5/1990 |
| DE | 37 41 575 C2 | 6/1990 |
| DE | 39 39 998 C2 | 6/1991 |
| DE | 43 06 997 A1 | 9/1994 |
| DE | 197 19 438 A1 | 11/1997 |
| DE | 197 14 167 A1 | 10/1998 |
| DE | 197 53 456 A1 | 6/1999 |
| DE | 198 27 417 A1 | 12/1999 |
| DE | 198 52 056 A1 | 5/2000 |
| DE | 199 26 728 A1 | 12/2000 |
| DE | 199 42 459 A1 | 3/2001 |
| DE | 100 18 918 A1 | 11/2001 |
| DE | 100 18 918 C2 | 7/2002 |
| EP | 0 110 429 A2 | 6/1984 |
| EP | 0 231 420 A1 | 8/1987 |
| EP | 0 268 347 A1 | 5/1988 |
| EP | 0 304 871 A2 * | 3/1989 |
| EP | 0 110 429 B1 | 1/1990 |
| EP | 0 231 420 B1 | 9/1991 |
| EP | 0 480 238 A1 | 4/1992 |
| EP | 0 268 347 B1 | 7/1992 |
| EP | 0 480 238 B1 | 7/1994 |
| GB | 1 044 753 | 10/1966 |
| GB | 1044753 | 10/1966 |
| GB | 1 509 245 | 5/1978 |
| JP | 11014624 A * | 1/1999 |
| JP | 11-228597 | 8/1999 |
| WO | WO 91/14000 A1 | 9/1991 |
| WO | WO 94/12877 A1 | 6/1994 |
| WO | WO 95/07286 A | 3/1995 |
| WO | WO 96/07103 A1 | 3/1996 |
| WO | WO 96/32647 A1 | 10/1996 |
| WO | WO 98/21583 A1 | 5/1998 |
| WO | WO 98/45406 A1 | 10/1998 |
| WO | WO 99/66831 A2 | 12/1999 |
| WO | WO 99/66831 A3 | 12/1999 |
| WO | WO 00/01350 A2 | 1/2000 |
| WO | WO 00/01350 A3 | 1/2000 |
| WO | WO 01/12237 A1 | 2/2001 |

OTHER PUBLICATIONS

Derwent Abstract: Ref. 1998-172444/16 zu JP 10033576 A.

Derwent Abstract: Ref. 1992-403005/49 zu JP 04299998 A.

Aass et al., "Microbiologic tests in epidemiologic studies: are they reproducible?" *Scand. J. Dent. Res.*, 1994, 102:355-360.

Dermer et al., *Ethylenimines and other Aziridines, Chemistry and Applications*, Academic Press, New York, New York (1969), Title page, Publication page, and Table of Contents (5 pgs).

DIN 53505, "Prüfung von Kautschuk und Elastomeren Harteprufung nach Shore A und Shore D," Mit DIN EN ISO 868:Jan. 1998 in German (5 pgs).

DIN EN ISO 4823, "Zahnheilkunde Elastomere Abformmassen (ISO 4823:2000) Deutsche Fassung EN ISO 4823:2000," Ersatz fur DIN EN 24823:Mar. 1994, ICS 11.060.10, in German (39 pgs).

Kneist et al., "Handelsübliche Speicheltests zum Mutans-Nachweis-Übersicht und Effizienzbewertung," *K. Quintessenz* (1999) 50(1): 33-43 in German.

Meyle et al., "Diagnostische Tests in der Parodontologie," Deutsche Zahnärztliche Zeitschrift, 1999, 54:73-77.

Patent Abstracts of Japan, vol. 1999, No. 13, Nov. 30, 1999, JP 11 228597 A (Taiho Yakuhin Kogyo KK), Aug. 24, 1999, Abstract (1 page).

Rupf et al., "Quantitative determination of *Streptococcus mutans* by using competitive polymerase chain reaction," *Eur. J. Oral Sci.*, 1999, 107:75-81.

DIN 53505, "Prüfung von Kautschuk und Elastomeren Härteprüfung nach Shore A und Shore D," Mit DIN EN ISO 8668:Jan. 1998 (in German) (5 pgs). (Also included is a translation in English, "Testing of rubber and elastomers Hardness testing according to Shore A and Shore D," German Standard, 1998, 8 pgs).

DIN EN ISO 4823, "Zahnheilkunde Elastomere Abformmassen (ISO 4823:2000) Deutsche Fassung EN ISO 4823:2000," Ersatz für DIN EN 24823:Mar. 1994, ICS 11.060.10 (in German)(38 pgs). (Also included is a translation in English, "Dental Medical Science Elastomeric Impression Materials (ISO 4823:2000) German Version EN ISP 4823:2000," German Standard, Aug. 2001, 42 pgs).

Kneist et al., "Handelsübliche Speicheltests zum Mutans-Nachweis-Übersicht und Effizienzbewertung," Die Quintessenz, 1999, 50(1):33-43 (in German). (Also included is a translation in English, "Commericial Saliva Tests for Mutans Detection—Overview and Efficacy Assessment," The Quintessenz, 1999, 11 pgs).

Meyle et al., "Diagnostische Tests in der Parodontologie," Deutsche Zahnarztliche Zeitschrift, 1999, 54:73-77 (in German). (Also included is a translation in English, "Diagnostic Tests in Periodontology," German Dental Magazine, 1999, 9 pgs).

* cited by examiner

SUPPORT MATERIALS AND IMAGING METHOD FOR INTRAORAL DIAGNOSTIC PURPOSES

This application is the national phase under 35 U.S. C. § 371 of PCT International Application No. PCT/EP00/05418 which has an International filing date of Jun. 13, 2000, which designated the United States of America.

The invention relates to deformable, curable or film-forming support materials which contain diagnostically useful additives for intraoral diagnostics. Furthermore, the invention relates to a process for the preparation of images for intraoral locus- and substance-specific diagnostic purposes as well as a process for the multiple and locus- and substance-specific investigation using the curable or film-forming support materials containing diagnostically useful additives. Such additives make it possible for the person skilled in the art to prepare images for intraoral locus- and substance-specific detection of pathogenic substances and/or of microorganisms or for intraoral locus- and substance-specific detection of substances which indicate mouth diseases or healing processes.

The invention relates in particular to dental impression materials for intraoral diagnostics, which contain diagnostically useful additives as well as a process for the application of diagnostically useful additives to cured impression materials, the diagnostically useful additives being suitable for intraoral locus- and substance-specific detection of pathogenic substances and/or of microorganisms or for intraoral locus- and substance-specific detection of substances which indicate mouth diseases or healing processes.

The invention also relates to deformable or curable or film-forming support materials, in particular dental impression materials which can locus-specifically absorb intraoral substances, these absorbed intraoral substances allowing the person skilled in the art to carry out test processes by applying diagnostically effective additives to the support materials which are suitable for intraoral locus- and substance-specific detection of pathogenic substances and/or of microorganisms, or for intraoral locus- and substance-specific detection of substances which indicate mouth diseases or healing processes.

The locus- and substance-specific detection of substances in the oral environment is a problem which has been worked on for a long time. Single-site tests are known to the person skilled in the art (e.g. EP-A-0 304 871), all of which are based on taking individual samples from definite points in the oral cavity, for example gingival pockets, the surfaces of teeth or root canals of teeth. Subsequent analysis of these samples is carried out using very widely varying methods, depending on the question asked, and a distinction should be made between four general approaches:

1. The microbiological investigation often takes place after the samples have been incubated for several days in suitable culture media because the number of microorganisms originally present is not sufficient for a direct investigation. After the microorganisms have been multiplied the Colony-Forming-Units (CFU) are counted and the number of microorganisms present in the sample monitored (Kneist, S; Klein, C.; Rupf, S.; Eschrich, K. Quintessenz (1999) 50, 33–43). The vital microorganisms present in the sample can multiply under optimal conditions in these test systems. The examination result thus indicates the maximum possible pathogenic potential of the evaluated microorganisms, if the microorganisms selectively attached by definite culture media could multiply unhindered in the same way in the oral cavity.

However it is known that precisely such optimum growth conditions are not present in the oral cavity, so that the test result is therefore only conditionally meaningful.

Moreover, it must not be overlooked that a culture of pathogenic microorganisms is started by incubation of the samples which have to be treated in practice with corresponding precautionary measures to minimise risk. Special disposal is necessary. Along with these disadvantages the incubation method for microbiological investigation is expensive and very time-consuming.

2. Immunological methods provide a further general approach to microbiological investigation in Single-Site-Tests. In these methods monoclonal or polyclonal antibodies are used against surface structures or separated substances of microorganisms. Moreover inflammation processes can also be followed with corresponding antibodies for example. Reference can be made, for example, to WO-94/12877, US-5 665 559, WO-96/07103 and WO-96/32647.

In comparison to the incubation methods according to paragraph 1, the immunological methods according to paragraph 2 are more specific, faster and more economical. However they have distinct weaknesses with regard to reproducibility, caused, amongst other things, by the sample taken. For example, not only vital, but also considerable quantities of dead microorganisms are to be found in one plaque region. Depending on the sample taken, the ratio of dead to vital microorganisms can be different. As the antibodies cannot distinguish between vital and dead microorganisms, an unpredictable range of variation results in deduction of the existing pathogenic potential of the evaluated microorganisms (Aass, A. M.; Preus, H. R., Zambon, J. J., Gjermo, P. Scand J. Dent Res (1994) 102, 355–360).

3. The method with the highest sensitivity is based on Poly-Chain-Reaction technology (PCR). The smallest amounts of microorganisms can be detected with high specificity. However the PCR technology is time-consuming, complex, expensive and not simple to control (Rupf, S., Kneist, S.; Merte, K.; Eschrich, K. Eur. J. Oral. Sci (1999) 107, 75–81).

4. Some further methods have been described which use biochemical markers in order to diagnose mouth diseases. The contribution from J. Meyle, Deutsche Zahnärztliche Zeitschrift (1999) 54, 73–77) offers an overview. The meaningfulness of individual biochemical markers must be assessed discriminatively, taking clinical studies into consideration, and remains the preserve of the person skilled in the art. It must be stressed that determination by biochemical markers takes place using Single-Site methods. Reference is made for example to Patent Specification WO-98/21583. The auxiliary tools necessary here are characterized in that they bind the samples to be examined (WO-91/14000, EP-A-0 304 871, U.S. Pat. No. 5,725, 373). For each sample site one auxiliary tool has to be used and analysed individually.

In principle, all Single-Site methods known from the state of the art have the decisive disadvantage that an approximately complete description of the situation in the oral cavity can only be gained with a large number of individual samples. Paper swabs are frequently used for sampling, as these can be inserted into gingival pockets or root canals (U.S. Pat. No. 5,725,373, EP-A-0 304 871).

It is known that the parodontitis activity from one gingival pocket to another in a patient can be very different, although the parodontitis exciter is located ubiquitously in the gingival pockets. Far more than 25 individual samples therefore have to be taken for one investigation and examined without it being possible to be sure that one or other focus of parodontitis does not remain unconsidered.

In principle, this shows that spot checks only allow unsatisfactory descriptions of the situation in the oral cavity. The time-consuming and expensive nature of single-site techniques can thus be only partly justified, and consequently single-site techniques have not found wide application in oral-cavity diagnostics.

For a long time there has therefore been an urgent need to make available a simple and economical process for simultaneous multiple as well as locus- and substance-specific intraoral investigation in the oral cavity.

The object of the present invention is to provide agents and methods for intraoral locus- and substance-specific, and at the same time, multiple detection of pathogenic substances and/or of microorganisms or of intraoral locus- and substance-specific detection of substances, which indicate mouth diseases or healing processes.

In the course of the description of the invention by pathogenic substances and/or microorganisms to be detected, or substances which indicate mouth diseases or healing processes is meant, for example, the following:
1. Metabolic products of bacteria, viruses or fungi, for example antigens, lipids, proteins, peptides, polysaccharides, DNA, RNA, sugars, amino acids, carboxylic acid, for example lactic acid and propionic acid, as well as other low molecular, anionic, cationic, or neutral substances and combinations of these, which result for example from ionic, polar, nonpolar, hydrophobic, covalent or adhesive interactions.
2. Surface structures of bacteria, viruses or fungi, consisting for example of antigens, lipids, proteins, peptides, polysaccharides, DNA, RNA, sugars, amino acids or other low molecular, anionic, cationic or neutral substances and combinations of these, which result for example from ionic, polar, nonpolar, hydrophobic, covalent or adhesive interactions.
3. Human or animal substances which are formed in response to infections by bacteria, viruses or fungi, consisting for example of antibodies, antigens, lipids, proteins, peptides, polysaccharides, DNA, RNA, sugars, amino acids or other low molecular, anionic, cationic or neutral substances and combinations of these, which result for example from ionic, polar, nonpolar, hydrophobic, covalent or adhesive interactions.
4. Human or animal substances, which indicate mouth disease which are not caused a priori by a bacterial, virus or fungus infection (for example, cancers) consisting for example of antibodies, antigens, lipids, proteins, peptides, polysaccharides, DNA, RNA, sugars, amino acids or other low molecular, anionic, cationic or neutral substances and combinations of these, which result for example from ionic, polar, nonpolar, hydrophobic, covalent or adhesive interactions.
5. Substances which are found in structures which are known to be the result of or the precondition for the occurrence of mouth diseases, for example plaque or biofilm, consisting for example of antibodies, antigens, lipids, proteins, peptides, polysaccharides, DNA, RNA, sugars, amino acids or other low molecular, anionic, cationic or neutral substances and combinations of these, which result for example from ionic, polar, nonpolar, hydrophobic, covalent or adhesive interactions.
6. Substances which indicate current healing processes, which are known to be the result of oral diseases or injuries, for example tissue and/or bone regeneration, consisting for example of antibodies, antigens, lipids, proteins, peptides, polysaccharides, DNA, RNA, sugars, amino acids or other low molecular, anionic, cationic or neutral substances and combinations of these, which result for example from ionic, polar, nonpolar, hydrophobic, covalent or adhesive interactions.

The substances listed above are examples of such substances which can be used alone or in combination for the purpose of diagnosing intraoral diseases and are described below as marker compounds.

According to the invention the object described is achieved by deformable, curable or film-forming support materials, which bind/absorb marker compounds, so that the diagnosis takes place for example on or in the support material. The invention relates to deformable, curable or film-forming support material, which is characterized in that it contains additives diagnostically useful for the locus- and substance-specific intraoral diagnosis which lead to a diagnostic result without a cultivation step. The diagnostically useful additives are used in particular for intraoral locus-specific detection of pathogenic substances and/or of micro organisms or for intraoral locus-specific detection of substances which indicate mouth diseases or healing processes. The additives can be present in the microcapsulated form. The support materials should contain at least enough diagnostic additives for a diagnostic signal to be observed.

The invention further relates to a process for the preparation of images for intraoral locus- and substance-specific diagnostic purposes, which is characterized in that diagnostically useful additives are applied to deformable, curable or film-forming support materials that contain no diagnostically useful additives, in such a quantity that a diagnostic signal can be observed, the additives leading to a diagnostic result without a cultivation step.

The invention also relates to processes for simultaneous multiple as well as locus- and substance-specific intraoral investigation, including the steps: Taking of impression with deformable, curable or film-forming support material, which contains diagnostically effective additives, and possible application of further diagnostically effective additives, or taking of impression with deformable, curable or film-forming support material, which contains no diagnostically effective additives, and application of diagnostically effective additives.

The diagnostically useful additives which can be used according to the invention are partly commercially available and can if necessary be physically, chemically, biochemically or genetically modified; this also applies in particular to enzymes and their substrates, to antibodies and their antigens and to oligonucleotides and polynucleotides.

The diagnostically useful additives allow the person skilled in the art to carry out diagnostic test processes which are suitable for intraoral locus- and substance-specific detection of pathogenic substances and/or of microorganisms, or which are suitable for intraoral locus- or substance-specific detection of substances which indicate mouth diseases or healing processes.

The mouth diseases which can be diagnosed include caries, early onset parodontitis, prepubertal parodontitis, juvenile parodontitis, rapid progressive parodontitis (RPP), adult parodontitis, refractory parodontitis, gingivitis, halitosis, infections with *Candida albicans, Candida krusei, Candida glabrata, Candida iusitaniae, Candida dubliniensis* and cancer.

Bacteria can be located in gingival pockets which release the sulphur found in cysteine or methionine in the form of volatile sulphur compounds such as mercaptans or hydrogen sulphide. Dissimilation active sulphate-reducing bacteria are known, whose hydrogen sulphide formation is correlated with sulphate reduction. By use of the support materials according to the invention and application of the process according to the invention, the rate of formation of hydrogen sulphide and mercaptans, preferably methyl mercaptans, can be measured in gingival pockets. Moreover, the bacterial enzyme activities, preferably methionin-γ-lyase, particularly preferably cysteine desulfhydrase, which catalyse the formation of the volatile sulphur compounds, can be used as a measure of halitosis activity in gingival pockets. Moreover the presence of the bacteria responsible for the release, preferably *fusobacteria, Porphyromonas, Veillonella, Clostridium* and *Treponema*, can be determined with polyclonal antibodies and their subclasses or monoclonal antibodies.

The different forms of parodontitis are causally connected with infection by *Actinobacillus actinomycetemcomitans, Bacterioides forsythus, Campylobacter rectus, Capnocytophage ochracea, Capnocytophage gingivalis, Elkenella corrodens, Fusobacterium nucleatum, Porphyromonas asaccharolyticus, Porphyromonas gingivalis, Prevotella dentalis, Prevotella intermedia, Prevotella nigrescens* and *Treponema denticola*. By use of the support materials according to the invention and application of the process according to the invention, the presence and quantity of bacteria in the sulcus fluid can be determined. Specific polyclonal antibodies and their subclasses or monoclonal antibodies which are directed against surface antigens of these bacteria, for example fimbriae, extra-cellular polysaccharides and adhesins are suitable for this purpose.

By use of the support materials according to the invention and application of the process according to the invention, enzyme activities can be measured in the sulcus fluid, indicating the presence and metabolic activity of a bacterium or a group of the named bacteria. Trypsin-like protease activity, preferably dipeptidyl peptidase activity, particularly preferably Arg-Gingipain activity and Lys-Gingipain activity, is used diagnostically. Synthetic peptides which contain at least one Arg radical (in P1 position) next to the detectable parting group can be used to determine Arg-Gingipain activity. Synthetic peptides which contain at least one Lys radical (in P1 position) next to the detectable parting group can be used for determining the Lys-Gingipain activity. Besides p-nitroaniline derivatives, for example Nα-benzoyl-DL-arginine-p-nitroanilide, and 2-naphthylamine-peptide derivatives, for example Nα-benzoyl-DL-arginine-β-naphthylamide, 6-aminoquinoline-peptide derivatives, rhodamine-peptide derivatives and coumarin-peptide derivative, for example 7-amido-4-methylcoumarin, such as N-t-Boc-Val-Pro-Arg-7-amido-4-methylcoumarin and 7-amino-4-chloromethylcoumarin, such as N-t-Boc-Val-Pro-Arg-7-amido-4-chloromethylcoumarin can be used as detectable parting groups.

By use of the support materials according to the invention and application of the process according to the invention the bacterial substances which lead to induction of cytokines can be diagnosed with polyclonal antibodies and their subclasses or monoclonal antibodies. Antibodies against lipopolysaccharides, lipoarabinomannan, peptidoglycans, teichoic acid derivatives, extra-cellular polysaccharides and lipid A are preferred.

By use of the support materials according to the invention and application of the process according to the invention the cytokinine formation induced by parodontitis exciters can be diagnosed with polyclonal antibodies and their subclasses or monoclonal antibodies. Antibodies against the interleukines IL-1, IL-2, IL-3, IL-4, IL-5, IL-6, IL-7, IL-8, tumour necrosis factor TNFα, interferons α, β, γ, colony-forming factors M-CSF, growth factors EGF, TGFα and chemokines MCP can be used.

By use of the support materials according to the invention and application of the process according to the invention, the destruction of the parodontal tissue by the enzyme activity of alkaline phosphatase, arylsulphatase, aspartataminotransferase, β-glucuronidase, cathepsins (G, B, D), elastase, hyaluronidase, lactate-dehydrogenase, lysocyme, matrix metal proteinases (collagenases, gelatinases), tissue inhibitor metal proteinases (TIMP), stomelysin, lactoferrin, tryptase and myeloperoxidase can be diagnosed.

By use of the support material according to the invention and application of the processes according to the invention the molecular markers for gingivitis can be diagnosed with polyclonal antibodies and their subclasses or monoclonal antibodies. These include cytokines, for example interleukines IL-1, IL-2, IL-4, IL-6, TNFα and arachidoic acid derivatives, for example prostaglandin $E_2$.

Caries is casually connected with infection by *Streptococcus salivarius salivarius, Streptococcus vestibularis, Streptococcus thermophilius, Streptococcus mutans, Streptococcus rattus, Streptococcus sobrinus, Streptococcus cricetus, Streptococcus downei, Streptococcus macacae, Streptococcus ferus, Streptococcus milleri, Streptococcus anginosus, Streptococcus constellatus, Streptococcus intermedius, Streptococcus mitis, Streptococcus oralis, Streptococcus sanguis, Streptococcus gordonii, Streptococcus parasanguis, Streptococcus crista, Streptococcus mitior, Lactobacillus acidophilius, Lactobacillus alimentarius, Lactobacillus brevis, Lactobacillus buchneri, Lactobacillus casei, Lactobacillus paracasei* ss *paracasei, Lactobacillus paracasei* ss *rhamnosus, Lactobacillus paracasei* ss *tolerans, Lactobacillus delbrueckii, Lactobacillus delbrueckii* ss *lactis, Lactobacillus delbrueckii* ss *delbrueckii, Lactobacillus delbrueckii* ss *bulgaricus, Lactobacillus endocarditis, Lactobacillus fermentum, Lactobacillus gasseri, Lactobacillus pseudoplantarum, Lactobacillus rhamnosus, Lactobacillus salivarius, Actinomyces israelii, Actinomyces odontolyticus, Actinomyces actinomycetemcomitans, Elkenella, Branhamella catarrhalis, Veillonella alcalescens, Veillonella parvula, Actinomyces naeslundii, Rothia dentocariosa*. By use of the support materials according to the invention and application of the process according to the invention the presence and the amount of cariogenic bacteria can be diagnosed with polyclonal antibodies and their subclasses or monoclonal antibodies, which are directed against the different surface antigens of these bacteria, for example proteins, lipopolysaccharides, glycoproteins, fimbriae, extracellular polysaccharides, adhesions, lipoteichoic acid derivatives, glucan-binding proteins, and collagen-binding proteins.

By use of the support materials according to the invention and application of the process according to the invention extra-cellular enzyme activity of cariogenic bacteria can be diagnosed, for example proteases, preferably glucosyltransferases, glucanase, fructosyltransferase, fructanase.

By use of the support materials according to the invention and application of the process according to the invention metabolic products of cariogenic bacteria can be diagnosed, for example butyric acid, formic acid, preferably acetic acid, propionic acid, and particularly preferably lactic acid. The acidification of the surrounding environment which accompanies acid release can in addition be detected using pH indicators, for example bromo phenol blue, Congo red, bromo cresol blue, preferably rhodol derivatives, particularly preferably Oregon green derivatives. As a result of the acidification of the pH in the surrounding environment, such as plaque, calcium ions are released from the hard dental substance. By use of the support materials according to the invention and application of the process according to the invention, this process can be diagnosed using calcium indicators, for example calcium crimson, preferably calcium green, calcium orange, and particularly preferably calcium Oregon green 488 BAPTA.

By use of the support materials according to the invention and application of the process according to the invention, the increase or decrease in the abovementioned marker compounds can be used as a measure of the healing process.

The list of the marker compounds is given by way of example and does not limit the invention.

It is surprising that in spite of the dynamic processes taking place in the oral cavity, which are subject to a constant exchange of fluid due to the secretions of the salivary glands and the sulcus fluid, sufficiently high concentrations of marker compounds are obtained on the surfaces of the support materials according to the invention or in the support materials, which allow a safe diagnosis to be made within the framework of routine treatments.

It is advantageous that by using the support materials according to the invention or by application of the process according to the invention, an almost complete situation description of the oral cavity is possible without a large number of individual samples, as is archiving of the present clinical picture, with the use of addition-cross-linking silicon impression materials being of particular interest, as the impressions can be kept practically indefinitely. If necessary, for the purpose of archiving the present clinical picture, the impressions can also be recorded by means of photography, digital cameras, UV-VIS/fluorescence scanners and evaluated by means of image documentation software.

In addition it is advantageous that by using the support material according to the invention and application of the process according to the invention an almost complete situation description of the individual teeth is possible without a large number of individual samples, as is archiving of the present clinical picture. Besides occlusal chewing surfaces and vestibular, lingual, coronal, apical, cervical, gingival, incisal areas of a tooth, the interproximal areas between the teeth are also recorded by the marking definition of the support materials.

It is also advantageous that by use of the support materials according to the invention or the process according to the invention, fluid from the gingival pockets can if necessary be collected and taken for locus- and substance-specific diagnosis. An almost complete situation description of the individual parodontal pockets is thus possible without a large number of individual samples, as is archiving of the present clinical picture.

It is above all advantageous that the locus- and substance-specific intraoral diagnosis takes place in such a way that the diagnostically useful additives do not burden the patient because the emission of the diagnostically useful additives is avoided. The diagnostically useful additives are not modification substances which modify the processes occurring intraorally. Repeated use of the locus- and substance-specific intraoral diagnosis to monitor the treatment process is thus made possible.

It is furthermore advantageous that by use of the support materials according to the invention or the process according to the invention the time-consuming cultivation or incubation of pathogenic microorganisms is dispensed with, and thus the risk connected with the multiplication of pathogenic germs is also minimised. A particularly great advantage of the method according to the invention is that detection also succeeds if the concentrations of the substances to be detected in the imaging material are very low.

In addition it is advantageous that the diagnosis result from the impression can if necessary be transferred to a positive impression. This is possible for example with plaster, hydrogels, model silicons or similar substances. Assignment of the diagnosis signals in the impression to individual teeth is thus facilitated.

With the support materials according to the invention direct locus- and substance-specific detection of microorganisms on the teeth also succeeds without having to cultivate or incubate the microorganisms adhering to the support material. This means that it is not necessary, for example, to add nutrients to the support material, as described in U.S. Pat. No. 4 976 951.

Equally advantageous is the simplicity of the processes described, which, in the case of many diseases allows problem-free early recognition or early diagnosis at low cost, and without considerably additional expense to the therapist and the patient.

As support material, dental impression materials or films, each based on silicon, polyether-silicon, polyether, alginate or hydrocolloid can for example be considered. For some application areas, such as the diagnosis of caries, alginates, preferably without the addition of phosphates or pyrophosphates are used. Equally suitable as support materials are all other known plastics, for example polyethylenes, polypropylenes, poly(meth)acrylates, polyurethanes, polycarbonates, polysulphide, polyvinylchlorides or rubber. Moreover, hydrogels, for example polyvinylpyrrolidone- or polyvinylalcohol-based, are suitable as support material. Also suitable for carrying out the process according to the invention are dental plaster preparations, non-curable plastic compositions such as kneading masses or solid dispersions in liquids, for example pastes and similar masses of silicon, waxes, gelatine, starch, fats and the above named support materials.

The basis of may impression materials is formed by addition-cross-linking or condensation-cross-linking silicons, polyether silicons or polyethers. These materials have been described extensively in the state of the art, so it is superfluous to go into them in more detail here. Addition- or condensation-cross-linking silicons are for example described in U.S. Pat. No. 3,897,376, in EP-B-0 231 420 as well as in U.S. Pat. No. 4,035,453 which is mentioned there on page 3, and also in EP-A-0 480 238 (see in particular page 2, lines 3–26)and in EP-B-0 268 347. The disclosure of these documents should be included here by means of reference. Polyether silicons are described for example in DE-A-37 41 575 as well as in DE-A-38 38 587, among others, the disclosure of which should also be included here. Polyethers are described for example in DE-B-17 45 810, DE-A-43 06 997, DE-A-40 93 555, DE-C-25 15 593, DE-A-197 19 438 and U.S. Pat. No. 3,453,242, the disclosure of which should likewise be included here. Impression materials based on N-alkylaziridinopolyether are preferred.

Support materials based on polyether are particularly suitable. The compounds include for example the following components:

(A) 30 to 96.9999, preferably 40 to 88.99, particularly preferably 45 to 80.49 wt.-% of at least one N-alkylaziridinopolyether with a molecular mass in the range of 1,000 to 20,000 g/mol and an aziridino equivalent mass in the range of 500 to 8.000 g/equivalent.

(B) 1 to 10, preferably 1 to 5, particularly preferably 1.5 to 3 wt.-% starter substances, which are suitable to effect the curing of the N-alkylaziridinopolyethers, p0 (C) 1 to 50, preferably 5 to 45, particularly preferably 8 to 43 wt.-% organic diluting agents, (D) 1 to 50, preferably 5 to 40, particularly preferably 10 to 30 wt.-% modifiers, including fillers, dyes, pigments, thixotropes, flow improvers, polymeric thickeners, surfactants, fragrances, and flavourings.

(E) 0.0001 to 10 wt.-% preferably 0.01 to 1 wt.-% diagnostic additives.

Component (A) includes N-alkylaziridinopolyether, in which the polyether basic substances can be homopolymers of ethylene oxide, propylene oxide or tetrahydrofurane, statistic co- and terpolymers of the named monomers and/or block copolymers of ethylene oxide and propylene oxide.

Such starter substances according to component (B) are suitable for use in two-component impression materials, which facilitate curing of the mixed preparation into an elastic solid body within a period of 1 to 20 minutes, this solid body meeting the requirements of an elastic impression material according to DIN/EN 2482 and having a Shore A hardness (DIN 53505) of at least 20 after 24 hours storage time.

Many of the known starters can be used as starters of the catalyst components. Expedient use is made of such starters or starter systems which allow simple adjustment of the curing process, produce no side effects and make it possible to reproduce the mechanical properties at the required level.

In DE-C-914 325 the use of oxonium, ammonium and sulphonium salts as starter substances is suggested.

A summary representation of the starter substances used for the curing of N-alkylaziridino compounds is contained in O.C. DERMER, G. E. HAM, "Ethylenimines and other Aziridines" Academic Press (1969).

A large number of compound classes and compounds have accordingly proved to be suitable in principle as polymerisation triggers. In the practical application of the cationic polymerisation of aziridinopolyethers, it is however very difficult to adjust the desired setting process with a sufficiently long processing time and rapid final curing. This aim can be achieved by the use of special trialkylsulphonium salts as described for example in EP-A-0 110 429.

By using special trisalkylsulphonium salts, the criteria of the curing speed and the properties of the elastic solid body can in principle be achieved.

In the patent application DE-A-100 18 918 starters are described which give the catalyst component only a low acid level and allow an easily adjustable, relatively long processing time after mixing of the basic components and catalyst components has been carried out.

Starter systems of this type are suitable for curing the base pastes at the necessary speed. By using these the desired properties of the elastic solid body can be achieved.

Patent application DE-A-199 42 459 describes elastomeric materials with improved catalyst components which are characterized by increased extensibility. According to this invention boric acid complexes are used as starters. These starters have proved their worth particularly for curing of N-alkylaziridinopolyethers.

As organic diluting agents, corresponding to components (C), polyetherpolyols, such as polypropylene glycols or mixed polyetherols with tetrahydrofurane and/or ethylene oxide and/or propylene oxide units, polyester polyols, such as polycaprolactondiols and polycaprolactontriols, polycarbonate, diols, aliphatic esters, oils, fats, waxes, aliphatic hydrocarbons, araliphatic hydrocarbons as well as mono- or polyfunctional esters of multivalent acids, such as phthalic acid or citric acid or esters or amides of alkylsulphonic acids and arylsulphonic acids are used.

The modifiers according to component (D) are mostly fine fillers, such as alumosilicates, precipitation silicic acids, silica dust, wollastonite, mica dust and diatomaceous earth, as well as dyes and pigments, the addition of which allows better assessment of the mixture quality and reduces the danger of confusion, thixotropes, such as finely dispersed silicic acids and other additives influencing flow behaviour, such as polymeric thickeners, and also surfactants for adjustment of the flow behaviour as well as fragrances and flavourings.

A further possible support material can also be a polymerisable liquid or a solution of a polymeric substance, which is sprayed or applied, for example painted, onto the places to be examined. Typically, this involves nitrocellulose-based paints with a volatile solvent as well as optionally further auxiliaries which cure to form a solid layer which can be removed from the substrate after absorption of the marker compound. In general, all polymers can be used which can be dissolved in suitable slightly volatile solvents. The use of polyurethanes in acetone is for example known. Suitable film-forming systems are sufficiently known from paints and varnish chemistry.

Firstly, the support material according to the invention can intraorally, locus-specifically absorb the marker compounds to be examined. The marker compound is detected, quantified or diagnostically evaluated on or in the support material locus- and substance-specifically in a subsequent procedure, with the marker compound also being able to be formed only as the result of a catalytic, chemical, or biochemical reaction. The marker compound to be analysed can for example be locally fixed on or in the support material by means of ionic, polar, nonpolar or hydrophobic interactions. The formation of microstructures and/or micro-spaces in the support materials, for example in the form of foams, can support the absorption and fixing of the marker compounds to be examined.

In a preferred embodiment, the support material contains at least one component or, to simplify the diagnostic procedure, all the necessary components of the diagnostic test system. These diagnostic additives can for example be locally fixed on or in the support material by means of ionic, polar, nonpolar or hydrophobic interactions. A local fixing or diagnostic additives is also made possible by the fact that the diagnostic additives are first fixed on high-molecular carriers and then kneaded into the support material. By this means the diffusion movement of the diagnostic additives in the support material is controlled. The formation of microstructures and/or micro-spaces in the support materials, for example in the form of foams, can support the absorption and fixing of the components. The components can be freely available in the support materials according to the invention, or be present in another phase.

The support materials according to the invention contain 0.0001 to 10 wt.-%, preferably 0.01 to 1 wt.-% diagnostic additives, however at least so many additives that the desired effect can be observed. In the case of application of the process according to the invention, diagnostic additives have to be applied to the support materials in such a quantity that the desired effect can be observed.

Desired effects can all be observable signals. These include, for example, colour signals, for example fluorescent, UV, VIS, phosphorescent or luminescent signals, which if necessary have to be detected with special equipment. Likewise, application of the process according to the invention can produce signals which can be observed by means of thermography, spectroscopy, chromatography, or by analysis of changes in the topography of the support materials.

Examples of diagnostic additives are, without meaning the following list to be understood as limiting the present invention:

dye indicators, for example pH indicators, such as bromo phenol blue, Congo red, bromo cresol green, Oregon green derivatives, rhodol derivatives, redox indicators, such as methylene blue, 5-cyano-2,3-ditolyltetrazolium chloride (CTC), 2-(4-iodophenyl)-3-(4-nitrophenyl)-5-phenyl-2H-tetrazolium chloride (INT), 8-dimethylamino-2,3-benzophenoxazine (Meldola's blue), 1-methoxyphenazine methosulphate (MPMS), 5-(3-carboxymethoxyphenyl-2-(4,5-dimethylthiazolyl)-3-(4-sulphophenyl)tetrazolium (MTS), 3-(4,5-dimethylthiazol-2-yl)-2,5-diphenyltetrazolium bromide (MTT), 3,3'-(3,3'-dimethoxy-4,4'-biphenylene)-bis[2-(4-nitrophenyl-5-phenyl)]-2H-tetrazolium chloride (NBT), nitrotetrazolium violet (NTV), phenazinmethosulphate (PMS), sodium-3'-[1-[(phenylamino)carbonyl]-3,4-tetrazolium]bis(4-methoxy-6-nitro)benzenesulphonic acid (XTT), phenazinethosulphate (PES), WST-1)

Fluorescence indicators, for example Oregon green 488 BAPTA, calcium green, calcium orange, calcium crimson, Chemoluminescence indicators, Vitality indicators, for example 5-bromo-2'-deoxyuridine, Other dye indicators, for example p-nitroaniline derivatives 2-naphthylamine derivatives, 7-amino-4-methylcoumarin derivatives, 7-amino-4-chloromethylcoumarin derivatives, 6-aminoquinoline derivatives, rhodamine derivatives, 5,5'-dithiobis-(2-nitrobenzoic acid), monobrombiman derivatives, tetramethylrhodamine derivatives, eosine derivatives, erythrosine derivatives, Texas red derivatives, coumarin derivatives, pyridyloxauzol derivatives, benzofurazan derivatives, naphthaline derivatives, didansyl cysteines, dansyl derivatives, aziridine derivatives, pyrene derivatives, Coomassie blue)

Moreover, the indicator substances can for example be covalently bound to enzymes, proteins, glycoproteins, lipopolysaccharides, polysaccharides, polyclonal and monoclonal antibodies, DNA, RNA cell organelles or microorganisms.

By diagnostic additives are also meant antibodies which are directed against marker compounds, such as polyclonal antibodies and their subclasses, and monoclonal antibodies. Moreover, the antibodies can be covalently bound for example to enzymes, proteins, glycoproteins, lipopolysaccharides, polysaccharides, DNA, RNA, cell organelles, microorganisms or other support materials.

Diagnostic additives can be enzymes of the following classes, the following list being by way of example, and not limiting the invention:

Oxidoreductases and their subclasses, for example dehydrogenases, such as lactate dehydrogenase, oxidases, peroxidases, reductases, monooxygenases, dioxygenases;

transferases and their subclasses, for example $C_1$-transferases, glycosyl transferases, such as glusoyltransferases, fructosyltransferases, aminotransferases, phospho-transferases;

hydrolases and their subclasses, for example esterases, glycosidases such as glucanase, fructanase, peptidases, for example dipeptidylpeptidases, Arg-gingipain, Lys-gingipain, collagenases, gelatinases, cathepsines, elastases, amidases, Lyases and their subclasses, for example C—C-lyases, C—O-lyases, C—N-lyases, C—S-lyases, Isomerases and their subclasses, for example epimerases, cis-trans-isomerases, intramolecular transferases;

Ligases and their subclasses, for example C—C-ligases, C—O-ligases, C—N-ligases, C—S-ligases.

2000 different enzymes are known today. A system has been developed for their classification which takes effect- and substrate-specificity into account. According to this, specific substrates and/or coenzymes (NAD(P), NAD(P)H, FAD, FMN, liponamide, ubiquinon, heme, ATP, ADP, AMP, GTP, GDP, GMP, UTP, UDP, UMP, CTP, CDP, CMP, coenzyme A, thiamindiphosphate, pyridoxalphosphate, biotin and tetrahydrofolate belong to each enzyme. These specific substrates and/or coenzymes have to be present as diagnostic additives if for example one or more enzymes serve as a marker substance. Conversely, it is of course true that specific enzymes can be used as diagnostic additives if specific substrates, for example sugar phosphates, lactic acid/lactate, pyruvate, acetic acid/acetate, propionic acid/propionate, formic acid/formiate, peptides and synthetic peptides serve as marker substances.

In addition the enzymes can be covalently bound to the support material.

Diagnostic additives can also be substances which have to be present concomitantly, in order to be able to diagnose the marker substances. Such substances include:

Buffers, for example sodium phosphate, sodium hydrogen phosphate, sodium dihydrogen phosphate, potassium phosphate, potassium hydrogen phosphate, potassium dihydrogen phosphate, sodium pyrrophosphate, sodium carbonate, potassium carbonate, sodium hydrogen carbonate, potassium hydrogen carbonate, sodium tetraborate, acetic acid/acetate, citric acid/citrate, diethylbarbituric acid, tris(hydroxymethyl)aminomethane (TRIS), glycine, glycylglycine, N-(2-acetamido)-2-aminoethane sulphonic acid (ACES), N-(2-acetamido) imminodiacetate (ADA), N,N-bis(2-hydroxyethyl)-2-aminoethane sulphonic acid (BES), N,N-bis(2-hydroxyethyl)glycine (BICINE), 2,2-bis-(hydroxyethyl)-iminotris(hydroxymethyl)methane (BIS-TRIS), 2-(cyclohexylamino)ethane sulphonic acid (CHES), 2-[4-(2-hydroxyethyl-1-piperazine)] ethane sulphonic acid (HEPES), 3-[4-(2-hydroxyethyl-1-piperazinyl)]propane sulphonic acid (HEPPS), 2-morpholinoethane sulphonic acid (MES), 3-morpholinopropane sulphonic acid (MOPS), piperazine-1, 4-bis(2-ethane sulphonic acid (PIPES), N-[tris(hydroxymethyl)-methyl]-2-aminoethane sulphonic acid (TES), N-[tris(hydroxymethyl)-methyl]-glycine (TRICINE);

Acids, for example sulphuric acid, sulphurous acid, phosphoric acid hydrochloric acid, acetic acid, nitric acid Bases, for example sodium hydroxide, potassium hydroxide, lithium hydroxide, ammonia, calcium hydroxide, magnesium oxide;

Solvents, for example water, methanol, ethanol, isopropanol, propanol, glycerine, dimethylsulphoxide, tetrahydrofuran, acetone, butanone, cyclohexane, toluene, methylene chloride, chloroform, alkanes, acetic acid ethyl esters;

Salts, for example magnesium chloride, magnesium sulphate, magnesium nitrate, calcium chloride, calcium sulphate, calcium nitrate, ferric (III) chloride, ferric (II)

chloride, zinc chloride, zinc sulphate, nickel chloride, manganese chloride, ammonium sulphate, sodium sulphate, sodium chloride, potassium chloride, sodium phosphates, potassium phosphates;

Other substances, for example glutathione, bovine serum albumin, sucrose, glucose, fructose, trehalose, polyethylene glycol, polyvinylpyrrolidone, hydrogen peroxide.

In a special embodiment of the invention, the diagnostic additives can be present in micro-encapsulated form. A number of molecules of diagnostic additives can be included in one microcapsule. The potentiating effect that occurs when micro-encapsulated diagnostic substances are used is a particular advantage.

Generally, when using multicomponent diagnostic systems according to the invention, i.e. systems in which the components necessary for detection are stored in several components, the individual components can be present separated from one another, but in each case enclosed in microcapsules, or even partly micro-encapsulated and partly free. Of course it also possible, with diagnosis systems involving more than two components, for at least two components in each case to be micro-encapsulated and for at least one other component to be kept available free in the support material. In each case it is essential only that a reaction of the diagnostic additives for the desired end product is prevented by keeping the individual components separate until one reaction partner is released by destruction of the microcapsule wall.

As impression materials are normally available as two components, it can be advantageous to keep different components of the active ingredients in different components of the impression materials, namely the base and the catalyst paste, microcapsulated or free.

When choosing suitable support materials care must be generally be taken that these are compatible with the diagnostic substances. For example when using fluorescent dyes, naturally the support materials must not contain components which are themselves fluorescent in the relevant wave length range. The requirement for inert support materials for diagnostic purposes is self-evident to the person skilled in the art and can be borne in mind by the person skilled in the art without problems.

The invention is explained below in more detail by means of examples, without these limiting it in any way.

APPLICATION EXAMPLE 1

Detection of Arg-Gingipain Via a Polyether Impression Material

A base paste was prepared in a standard laboratory three-fingered kneader, 53.2 parts by weight of an aziridinopolyether obtained according to Example 12 of DE-PS-17 45 810 being mixed with 18.1 g of a hydrogenated palm oil and 6.4 parts by weight dibenzyl toluene for the sake of homogeneity. This mass was combined with 11.8 parts of a copolymer of ethylene oxide and tetramethylene oxide units of an average molar mass of 6500, as well as 0.1 parts laurylimidazol and 5.0 parts of a block copolymer of ethylene oxide and propylene oxide units with an average molecular mass of 3500. This mass was then mixed with 5.3 parts by weight diatomaceous earth.

A catalyst paste was mixed by homogenisation of 33.8 parts by weight acetyltributylcitrate with 14.1 parts ethylene oxide-propylene oxide block copolymer and 19.0 parts of a sulphonium salt which was obtained according to Example 31 of DE-PS-25 15 593. This mass was combined with 11 parts diatomaceous earth and 20.5 parts pyrogenic silicic acid as well as 1 part titanium dioxide. Then 0.7 g tris (hydroxymethyl)aminomethane, 0.8 g glycylgycine and 200 µg N-t-Boc-Val-Pro-Arg-7-amido-4-methyl-coumarin were added as buffers.

Base and catalyst pastes were mixed in a volume ratio 5:1 and cured after approx. 8 minutes to produce a homogenous rubber. Doping of the surface of this rubber during the setting period with 2 µl Arg-gingipain-containing solution (original solution: 0.5 mg/ml Arg-gingipain in 200 mM tris(hydroxymethyl)aminomethane pH 7.6) resulted after a few minutes in an intense blue fluorescence emission at this point, at an excitation wave length of 360 nm.

APPLICATION EXAMPLE 2

Detection of Arg-gingipain on Alginate Test Pieces 20 ml solution containing 0.12 g tris(hydroxymethyl) aminomethane, 100 µg N-t-Boc-Val-Pro-Arg-7-amido-4-methylcoumarin, pH 7.6 were added to 10 g alginate (Palgat Plus Quick, ESPE Dental AG) and kneaded with a broad plastic spatula to produce a homogenous paste within 1 minute. During the setting period the alginate test piece was doped with 2 µl Arg-gingipain-containing solution (original solution: 0.5 mg/ml Arg-gingipain in 200 mM tris(hydroxymethyl)aminomethane, pH 7.6). After 5 minutes, an intense blue fluorescent emission could be observed at this point, at an excitation wave length of 360 nm.

APPLICATION EXAMPLE 3

Detection of Arg-gingipain Via an Alginate Impression Material in Gingival Pockets 40 ml solution containing 0.24 g tris(hydroxymethyl) aminomethane, 0.26 g glycylglycin, 200 µm N-t-Boc-Pro-Arg-7-amido-4-methylcoumarin was added to 20 g alginate (Palgat Plus Quick, ESPE Dental Ag) and kneaded with a broad plastic spatula to produce a homogenous mass within 1 minute. The alginate mass was placed in a commercially available impression tray and placed on the upper and lower jaw of a parodontitis patient for 5 minutes. Intense blue fluorescence emissions could be observed on individual gingival pocket edges at an excitation wave length of 360 nm.

APPLICATION EXAMPLE 4

Detection of Lactic Acid on Alginate Test Pieces 10 ml solution containing 0.065 g glycylglycin, 0.06 g tris(hydroxymethyl)aminomethane, 9 mg NAD, 0.23 mg phenazine methosulphate, 0.75 mg 3-(4,5-dimethylthiazol-2-yl)-2,5-diphenyltetrazolium bromide (MTT), and 463 units lactate dehydrogenase from pig's heart was added to 5 g alginate and kneaded with a broad spatula to produce a homogenous mass within 1 minute. The alginate test pieces were doped with 5 µl of a 10 mM calactate solution in 100 mM tris(hydroxymethyl)amino-methane, pH 9.0. After 4 minutes the development of a blue coloration could be observed at the doping point.

APPLICATION EXAMPLE 5

Determination of Lactic Acid Formation on Teeth by Means of an Alginate Impression Material 40 ml solution containing 0.26 g glycylglycin, 0.24 g tris(hydroxymethyl)aminomethane, 36 mg NAD, 0.9 mg phenazine methosulphate, 3 mg 3-(4,5-dimethylthiazol-2-yl)-2,5-diphenyltetrazolium bromide (MTT), and 1850 units lactate dehydrogenase form pig's heart was added to 20 g alginate and kneaded with a broad spatula to produce a homogenous mass within 1 minute. The alginate mass was placed in a commercially available impression tray and placed on the upper and lower jaw of a patient. The patient was supposed to have cleaned his teeth beforehand, rinsing with a 1% sucrose solution. After 4 minutes the impression tray was removed. Places where there was lactic acid formation could be identified from the blue coloration developing.

The invention claimed is:

1. A deformable, curable, or film-forming composition comprising:
    a deformable, curable or film-forming support material, wherein the support material comprises a material that is (i) an impression material or film based on silicon, polyether-silicon, polyether, alginate or hydrocolloid, (ii) a polyethylene, polypropylene, poly(meth)acrylate, polyurethane, polycarbonate, polysulphide or polyvinylchloride plastic, (iii) a rubber composition, (iv) a polyvinylpyrrolidone-based or polyvinylalcohol-based hydrogel, or (v) a dental plaster preparation; and
    at least one diagnostically useful additive for locus-specific and substance-specific intraoral diagnosis that provides such diagnostic result without a cultivation step and presents the diagnostic result by signal development in or upon the surface of the support material or by binding of a detectable agent to the support material, wherein at least one diagnostically useful additive is useful for intraoral locus-specific detection of pathogenic substances and/or microorganisms or for intraoral locus-specific detection of substances that indicate mouth diseases or healing processes.

2. The composition according to claim 1, in which the diagnostic additives are contained in a quantity of from 0.0001 to 10 wt.-%.

3. The composition according to claim 1, in which the diagnostic additives are contained in a quantity of from 0.01 to 1 wt.-%.

4. The composition according to claim 1 that is based upon N-alkylaziridinopolyether.

5. The composition of claim 1 in which at least one signal is development of a visible color, a fluorescent signal, an ultraviolet signal, a phosphorescent signal or a luminescent signal.

6. The composition of claim 1, in which the at least one diagnostically useful additive comprises an indicator selected from the group consisting of bromo phenol blue, Congo red, bromo cresol green, Oregon green derivatives, rhodol derivatives, redox indicators, such as methylene blue, 5-cyano-2,3-ditolytetrazolium chloride, 2-(4-iodophenyl)-3-(4-nitrophenyl)-5-phenyl-2H-tetrazolium chloride, 8-dimethylamino-2,3-benzophenoxazine, 1-methoxyphenazine methosulphate, 5-(3-carboxymethoxyphenyl)-2-(4,5-dimethylthiazolyl-3-(4-sulphophenyl)tetrazolium, 3-(4,5-dimethylthiazol-2-yl)-2,5-diphenyltetrazolium bromide, 3,3'-(3, 3'-dimethoxy-4,4'-biphenylene)-bis[2-(4-nitrophenyl-5-phenyl)]-2H-tetrazolium chloride, nitrotetrazolium violet, phenazinmethosulphate, sodium-3'-[1-[(phenylamino)carbonyl]-3,4-tetrazolium]bis(4-methoxy-6-nitro)benzenesulphonic acid, phenazinethosulphate, Oregon green 488 BAPTA, calcium green, calcium orange, calcium crimson, 5-brom-2'-deoxyuridine, a p-nitroaniline derivative, a 2-naphthylamine derivative, a 7-amino-4-methylcoumarin derivative, a 7-amino-4-chloromethylcoumarin derivative, a 6-aminoquinoline derivative, a rhodamine derivative, 5,5'-dithiobis-(2-nitrobenzoic acid), a monobrombiman derivative, a tetramethylrhodamine derivative, an eosine derivative, an erythrosine derivative, a Texas red derivative, a coumarin derivative, a pyridyloxauzol derivative, a benzofurazan derivative, a naphthaline derivative, a didansyl cysteine, a dansyl derivative, an aziridine derivative, a pyrene derivative and Coomassie blue.

7. The composition of claim 6 in which the indicator is covalently bound to an enzyme, a protein, a glycoprotein, a lipopolysaccharide, a polysaccharide, a polyclonal antibody, a monoclonal antibody, a DNA molecule, a RNA molecule, a cell organelle or a microorganism cell.

8. The composition of claim 1 in which the diagnostically useful additive is an enzyme selected from the group consisting of an oxidoreductase, a dehydrogenase, an oxidase, a peroxidase, a reductase, a monooxygenases, a dioxygenase, a transferase, a hydrolase, a lyase, an isomerase and a ligase.

9. The composition of claim 8 in which the diagnostically useful additive in an enzyme selected form the group consisting of lactate dehydrogenase, $C_1$-transferase, glycosyl transferase, glusoyltransferase, fructosyltransferase, aminotransferase, phospho-transferase esterase, a glycosidase, glucanase, fructanase, a peptidase, a dipeptidylpeptidase, Arg-gingipain, Lys-gingipain, a collagenase, a gelatinase, a cathepsin, an elastase, an amidase, a C—C-lyase, a C—O-lyase, a C—N-lyase, a C—S-lyase, an epimerase, a cis-trans-isomerase, an intramolecular transferase, a C—C-ligase, a C—O-ligase, a C—N-ligase, and a C—S-ligase.

10. The composition of claim , in which a plurality of diagnostically useful additives are present and each is micro-encapsulated.

11. The composition of claim in which a plurality of diagnostically useful additives are present and at least one is micro-encapsulated and at least one is free in the support material.

12. A deformable, curable, or film-forming composition comprising:
    a deformable, curable or film-forming support material; and
    at least one diagnostically useful additive for locus-specific and substance-specific intraoral diagnosis that provides such diagnostic result without a cultivation step and presents the diagnostic result by signal development in or upon the surface of the support material or by binding of a detectable agent to the support material, wherein at least one diagnostically useful additive is useful for intraoral locus-specific detection of pathogenic substances and/or microorganisms or for intraoral locus-specific detection of substances that indicate mouth diseases or healing processes and wherein at least one diagnostically useful additive is present in micro-encapsulated form.

13. A process for making an intraoral diagnostic material comprising applying to a deformable, curable or film-forming support material containing no diagnostically useful additives at least one diagnostically useful additive that is useful for intraoral locus-specific detection of pathogenic substances and/or microorganisms or for intraoral locus-specific detection of substances that indicate mouth diseases or healing processes, in a quantity effective for producing a diagnostic signal within or upon the surface of the support material or by binding of a detectable agent to the surface of the support material after the support material is applied to the oral cavity of a subject, wherein the support material comprises a material that is (i) an impression material or film based on silicon, polyether-silicon, polyether, alginate or hydrocolloid, (ii) a polyethylene, polypropylene, poly(meth)acrylate, polyurethane, polycarbonate, polysulphide or polyvinylchloride plastic, (iii) a rubber composition, (iv) a polyvinylpyrrolidone-based or polyvinylalcohol-based hydrogel, or (v) a dental plaster preparation.

14. The process according to claim 13 in which the diagnostically useful additives are present in micro-encapsulated form.

15. The process according to claim 13 or 14, in which the signal is development of a visible color, a fluorescent signal, an ultraviolet signal, a phosphorescent signal or a luminescent signal.

16. The process according to claim 13 or 14 in which the diagnostically useful additives are used in a quantity of 0.0001 to 10 wt.-%.

17. The process according to claim 16 in which the support material comprises:
(A) 30 to 96.9999 wt.-% of at least one N-alkylaziridinopolyether with a molecular mass in the range of 1,000 to 20,000 g/mol and an aziridino equivalent mass in the range of 500 to 8,000 g/equivalent,
(B) 1 to 10 wt.-% starter substances, which are suitable to effect the curing of the N-alkylaziridinopolyethers,
(C) 1 to 50 wt.-% organic diluting agents, and
(D) 1 to 50 wt.-% of at least one modifier, selected from the group consisting of fillers, dyes, pigments, thixotropes, flow improvers, polymeric thickeners, surfactants, fragrances, and flavourings.

18. The process according to claim 13 in which the support material is an impression material based on N-alkylaziridinopolyether.

19. A method for simultaneous examination of multiple intraoral loci for the presence of at least one specific substance comprising:
i) taking an impression of the oral cavity, or a part thereof, of a subject with a deformable, curable, or film-forming composition comprising:
a deformable, curable or film-forming support material; and
at least one diagnostically useful additive for locus-specific and substance-specific intraoral diagnosis that provides such diagnostic result without a cultivation step and presents the diagnostic result by signal development in or upon the surface of the support material or by binding of a detectable agent to the support material, wherein at least one diagnostically useful additive is useful for intraoral locus-specific detection of pathogenic substances and/or microorganisms or for intraoral locus-specific detection of substances that indicate mouth diseases or healing processes;
ii) optionally applying to the oral cavity or to the impression at least one further diagnostically effective additive; and
iii) obtaining a signal from said diagnostically effective additive(s) at multiple intraoral loci.

20. The method of claim 19, wherein the specific substance that is detected is one that is diagnostic for caries, early onset parodontitis, prepubertal parodontitis, juvenile parodontitis, rapid progressive parodontitis (RPP), adult parodontitis, refractory parodontitis, gingivitis, halitosis, infections with Candida albicans, Candida krusei, Candida glabrata, Candida iusitaniae, Candida dubliniensis or cancer.

21. The method of claim 19 in which the specific substance is a substance that induces one or more cytokines.

22. The method of claim 21 in which the diagnostically effective additive is a monoclonal or polyclonal antibody that specifically binds to a lipopolysaccharide, a lipoarabinomannan, a peptidoglycan, a teichoic acid derivative, an extracellular polysaccharide, lipid A, interleukin-1, interleukin-2, interleukin-3, interleukin-4, interleukin-5, interleukin-6, interleukin-7, interleukin-8, tumor necrosis factor $\alpha$, interferon $\alpha$, interferon $\beta$, interferon $\gamma$, colony-forming factors M-CSF, epidermal growth factor, transforming growth factor $\alpha$, the chemokine MCP, an arachidonic acid derivative, or prostaglandin $E_2$.

23. The method of claim 19, in which the diagnostically effective additive is a substrate for an enzyme selected from the group consisting of alkaline phosphatase, arylsulphatase, aspartataminotransferase, $\beta$-glucuronidase, cathepsin G, cathepsin B, cathepsin D, elastase, hyaluronidase, lactate-dehydrogenase, lysocyme, a matrix metal proteinase, a collagenase, a gelatinase, a tissue inhibitor of a metal proteinase, stomelysin, lactoferrin, tryptase and myeloperoxidase that produces a color reaction.

24. The method of claim 19, in which the diagnostically effective additive is a pH indicator or a calcium indicator.

25. The method of claim 19 in which the image is transferred to a positive impression.

26. A deformable, curable, or film-forming composition comprising:
a deformable, curable or film-forming support material; and
at least one diagnostically useful additive for locus-specific and substance-specific intraoral diagnosis that provides such diagnostic result without a cultivation step and presents the diagnostic result by signal development in or upon the surface of the support material or by binding of a detectable agent to the support material, wherein at least one diagnostically useful additive is used for intraoral locus-specific detection of pathogenic substances and/or microorganisms or for intraoral locus-specific detection of substances that indicate mouth diseases or healing processes,
wherein the composition is in the form of polymerizable liquid that can be applied by spraying into the oral cavity or painting upon a surface of the oral cavity.

27. A method for producing a diagnostic image of the oral cavity comprising:
i) applying to the oral cavity, or a part thereof, of a subject a deformable, curable, or film-forming composition comprising:
a deformable, curable or film-forming support material; and
at least one diagnostically useful additive for locus-specific and substance-specific intraoral diagnosis that provides such diagnostic result without a cultivation step and presents the diagnostic result by signal development in or upon the surface of the support material or by binding of a detectable agent to the support material, wherein at least one diagnostically useful additive is useful for intraoral locus-specific detection of pathogenic substances and/or microorganisms or for intraoral locus-specific detection of substances that indicate growth mouth diseases or healing processes;

optionally applying to the oral cavity or to the impression at least one further diagnostically effective additive; and iii) imaging the diagnostic signal(s) produced by the diagnostically effective additive(s) thereby producing a diagnostic image of the oral cavity.

28. A deformable, curable, or film-forming composition comprising:

a deformable, curable or film-forming support material, wherein the support material comprises a material that is (i) an impression material or film based on silicon, polyether-silicon, polyether, alginate or hydrocolloid, (ii) a polyethylene, polypropylene, poly(meth)acrylate, polyurethane, polycarbonate, polysulphide or polyvinylchloride plastic, (iii) a rubber composition, (iv) a polyvinylpyrrolidone-based or polyvinylalcohol-based hydrogel, or (v) a dental plaster preparation; and at least one diagnostically useful additive for locus-specific and substance-specific intraoral diagnosis that provides such diagnostic result without a cultivation step and presents the diagnostic result by signal development in or upon the surface of the support material or by binding of a detectable agent to the support material.

* * * * *

UNITED STATES PATENT AND TRADEMARK OFFICE
CERTIFICATE OF CORRECTION

PATENT NO. : 7,175,430 B1
APPLICATION NO. : 10/009603
DATED : February 13, 2007
INVENTOR(S) : Gasser et al.

It is certified that error appears in the above-identified patent and that said Letters Patent is hereby corrected as shown below:

In column 5, line 19, delete "*Elkenella*" and insert --*Eikenella*--;

In column 6, line 20, delete "casually" and insert --causally--;

In column 6, line 22, delete "*thermophilius*" and insert --*thermophilus*--;

In column 6, line 40, delete "*Elkenella*" and insert --*Eikenella*--;

In column 6, line 50, delete "adhesions" and insert --adhesins--;

In column 9, line 1, delete "p(0)";

In column 9, line 1, start a new paragraph at "(C)";

In column 9, line 7, delete "flavourings." and insert --flavourings,--;

In column 9, line 60, delete "components" and insert --component--;

In column 9, line 65, delete "polycarbonate, diols" and insert --polycarbonate diols--;

In column 11, line 31, delete "derivatives 2" and insert --derivatives, 2--;

In column 12, line 41, delete "imminodiacetate" and insert --iminodiacetate--;

In column 12, line 56, delete "nitric acid" and insert --nitric acid;--;

In column 13, line 34, delete "be"

In column 14, line 43, delete "Ag" and insert --AG--;

In column 15, line 10, delete "form" and insert --from--;

In column 16, line 24 (claim 8), delete "monooxygenases" and insert --monooxygenase--;

In column 16, line 27 (claim 9), delete "in" and insert --is--;

In column 16, line 27 (claim 9), delete "form" and insert --from--;

In column 16, line 37 (claim 10), delete "claim , in" and insert --claim 1, in--;

UNITED STATES PATENT AND TRADEMARK OFFICE
CERTIFICATE OF CORRECTION

PATENT NO.       : 7,175,430 B1
APPLICATION NO.  : 10/009603
DATED            : February 13, 2007
INVENTOR(S)      : Gasser et al.

It is certified that error appears in the above-identified patent and that said Letters Patent is hereby corrected as shown below:

In column 16, line 40 (claim 11), delete "claim in" and insert --claim 1, in--;

In column 17, line 43 (claim 19), delete "apart" and insert --a part--;

In column 18, line 42 (claim 26), delete "used" and insert --useful--;

In column 18, line 66 (claim 27), delete "growth";

In column 19, line 1 (claim 27), delete "optionally" and insert --ii) optionally--.

Signed and Sealed this

Twenty-seventh Day of November, 2007

JON W. DUDAS
*Director of the United States Patent and Trademark Office*